United States Patent [19]

Go et al.

[11] Patent Number: 4,467,132

[45] Date of Patent: Aug. 21, 1984

[54] AKLYLATION AID FOR SULFURIC ACID CATALYZED ALKYLATION UNITS

[75] Inventors: Ting S. L. Go, Houston; George R. Wilson, III, San Antonio, both of Tex.

[73] Assignee: Atlantic Richfield Company, Los Angeles, Calif.

[21] Appl. No.: 463,433

[22] Filed: Feb. 3, 1983

[51] Int. Cl.$^3$ ................................................. C07C 2/58
[52] U.S. Cl. ............................. 585/724; 585/728/731
[58] Field of Search ................ 585/723, 724, 731, 728

[56] References Cited

U.S. PATENT DOCUMENTS

| | | | |
|---|---|---|---|
| 2,286,184 | 6/1942 | Bradley et al. | 585/731 |
| 2,430,673 | 11/1947 | Gibson et al. | 585/731 |
| 2,981,772 | 4/1961 | Holzman | 585/731 |
| 3,046,318 | 7/1962 | Ayers et al. | 585/731 |
| 3,766,293 | 10/1973 | Parker et al. | 585/731 |
| 3,778,489 | 12/1973 | Parker et al. | 585/724 |

Primary Examiner—Delbert E. Gantz
Assistant Examiner—Cynthia A. Prezlock
Attorney, Agent, or Firm—C. R. Reap; J. C. Martin, Jr.; D. M. Kozak

[57] ABSTRACT

The efficiency of acid catalyzed alkylation of alkanes with olefins is improved by conducting the alkylation in the presence of small amounts of a neo acid.

16 Claims, No Drawings

AKLYLATION AID FOR SULFURIC ACID CATALYZED ALKYLATION UNITS

FIELD OF THE INVENTION

This invention relates to a process for alkylating hydrocarbons and more particularly to an improved process of alkylating aliphatic hydrocarbons, particularly branched-chain aliphatic hydrocarbons with olefinic hydrocarbons in the presence of a strong acid.

BACKGROUND

The value of hydrocarbons can often be enhanced by alkylation of lower hydrocarbons to produce higher molecular weight hydrocarbons. For example, isobutanes can be alkylated with isobutene to produce isooctane which is valuable for increasing the octane rating of gasoline. A common commercial method for alkylating a hydrocarbon is to react the hydrocarbon with selected olefins in the presence of a strong acid such as sulfuric acid. Unfortunately, such acid solutions are not readily miscible with organic liquids. Consequently, in alkylation processes catalyzed by strong acids, it has been necessary to use considerable excess acid to effect a commercially feasible degree of alkylation. The unused acid is discarded with the spent acid thereby reducing the efficiency of the process and augmenting the already burdensome waste disposal problem. Improvements which will reduce the amount of acid waste have long been sought.

PRIOR ART

In attempts to improve the efficiency of acid catalyzed alkylations reaction temperatures have been lowered, the mixing efficiency has been increased and the ratio of hydrocarbon to olefin has been varied. None of these techniques has meet with significant success.

Chemical approaches have also been attempted. For example, various chemicals have been added to acid-catalyzed alkylation reaction mixtures to promote more efficient use of the acid catalyst. Thus, U.S. Pat. No. 3,324,196, issued to Kramer et al, discloses the use of an amine or amide containing at least one $C_8$ to $C_{20}$ aliphatic group to promote the acid-catalyzed alkylation of aliphatic and aromatic hydrocarbons. U.S. Pat. No. 2,880,255 discloses the use of mercaptans or combinations of aliphatic amines and mercaptans to promote the alkylation of hydrocarbons.

The present invention is based on the use of chemical additives to promote alkylation reactions. It has been discovered that certain organic acids increase the efficiency of acid-catalyzed alkylation reactions. Accordingly, it is an object of the invention to present an improved alkylation process. It is another object of the invention to present an improved process for alkylating hydrocarbons with acid catalyst. It is another object of the invention to reduce the acid consumption in acid-catalyzed alkylation reactions. These and other objects of the invention are supported in the following description and examples of the invention.

SUMMARY OF THE INVENTION

It has now been discovered that the highly efficient alkylation of aliphatic hydrocarbons by means of strong acid catalysts can be effected by carrying out the alkylation reaction in the presence of at least one carboxylic acid having the structure

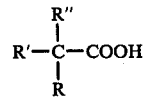

Wherein R, R' and, R" are alkyl groups and the average total sum of the carbon atoms in R, R' and, R" usually varies from 3 to about 20 or more. Acids having the above structure are often referred to generally as neo acids.

DETAILED DESCRIPTION

Neo acids useable in the invention are commercially available from Exxon Chemical Company under the name Neo Acids or from Shell Chemical Company under the name Versatic Acids ® or they may be prepared by methods such as described in the article "Neoacids" by Feffer, Journal of the American Oil Chemists Society, 55 342A (1978). The method of preparation of the neo acids is well known and forms no part of this invention.

The neo acid may be a pure acid or mixture of isomers of a neo acid or it may be a mixture of various molecular weight acids, such as the bottoms residue obtained after the purification step of a neo acids manufacturing process. The total number of carbon atoms in the alkyl radicals attached to the alpha carbon atom of these acids may range as high as 25 or more. The average of the total number of carbon atoms in the alpha alkyl radicals is desirably in the range of 3 to about 20 carbon atoms. When the neo acid is trimethyl acetic acid the sum of R', R" and R'''will, of course, be 3. Preferred neo acids are those in which the total numbers of carbon atoms in R, R' and R" is 3 to 8.

Typical neo acids that fall within the above description include neopentanoic acid, mixed neodecanoic acids, 2,2-dimethyl heptadecanoic acid, triethyl acetic acid, dimethyl pentyl acetic acid, etc. Preferred neo acids are trimethyl acetic acid and the pure or mixed neodecanoic acids.

The neo acid may be used in any acid-catalyzed alkylation reaction between hydrocarbons and olefins. Hydrocarbons which are often alkylated include saturated aliphatic and cycloaliphatic hydrocarbons and aromatic hydrocarbons. The neo acids are particularly useful for alkylating lower branched-chain alkanes, such as isobutane and isopentane with lower olefins to produce octane rating improving additives for gasoline. Lower alkanes which are desirably alkylated include those having 4 to 10 carbon atoms.

Olefins which are used in alkylation reactions include those monoolefins having 3 to 10 carbon atoms. The olefins may be straight-or branched-chain and the olefinic unsaturation may be located anywhere in the structure of the compound.

Particularly useful gasoline additives for increasing the octane rating are the branched octanes such as the compounds or mixture of compounds obtained when isobutane is alkylated with mixed butenes. Branched octanes can also be prepared by the reaction of other alkanes and olefins, for example by the reaction of isopentane and propylene.

Various strong acids are useful for catalyzing the alkylation of aliphatic or aromatic hydrocarbons with an olefin. Sulfuric acid, because of its efficiency and low cost is the most commonly used acid alkylation catalyst.

Other strong acids which can be used include hydrofluoric acid, phosphoric acid and fluorosulfonic acid. Any of the other well known strong acids are also useful for catalyzing alkylation reactions. Strong Lewis acids, such as aluminum bromide, aluminum chloride, antimony pentafluoride, antimony pentachloride, boron trifluoride, etc., can also be used as the acid catalyst in the process of this invention. In general, the alkylation promoters of the invention can be used with any known acid alkylation catalyst.

The alkylation reaction is carried out with all of the reactants in the liquid phase. The temperature of the reaction is that generally used for alkylation reactions. Reaction temperatures can vary from below 0° to as high as or higher than 200° F. The pressure of the reaction is not critical and any pressure which will maintain the reactants substantially in the liquid phase may be employed. Pressures generally range from atmospheric to as high as 1000 psi or higher.

The amount of neo acid promoter added to the reaction mixture usually varies from about 0.0005 to 5.0 percent, based on the total weight of catalyzing acid present in the reaction mixture. Amounts less than 0.0005 weight percent generally produce insignificant results and amounts greater than about 5.0 weight percent are generally unnecessary, although such higher concentrations can be used, if desired. The preferred neo acid lower concentration is about 0.001 percent and the most preferred minimum level is about 0.005 percent, based on the total weight of acid catalyst in the reaction mixture. The preferred upper limit of the neo acid concentration is about 1.0 percent and the most preferred upper limit is about 0.5 percent, based on the total weight of acid catalyzing agent in the reaction mixture. The optimum amount of neo acid will, of course, vary depending upon the particular neo acid or mixture of neo acids employed, the particular strong acid catalyst used and the particular hydrocarbons and olefins being reacted.

The alkylation promoters of the invention may be used with other additives, if desired. For example other alkylation promoters may be used in combination with the promoters of the invention or surfactants or other agents may be added to the reaction mixture.

In a typical application of the invention the hydrocarbon to be alkylated such as a lower branched-chain alkane and an olefin are introduced into a suitable alkylation reaction vessel at a controlled temperature, usually in the range of about 40° to 60° F., and at a pressure sufficiently high to maintain the reactants in the liquid state. The ratio of alkylatable hydrocarbon to olefin alkylating agent is preferably maintained at a high ratio, e.g. about 10:1, to minimize the amount of alkyl sulfate formed by the reaction of olefin with sulfuric acid. An acid alkylation catalyst, such as sulfuric acid, and the neo acid alkylation promoter are introduced into the reactor, perferably on a continuous basis. At the end of the desired reaction period the finished product is removed from the reaction vessel and separated from the spent acid. The reaction may be carried out on either a batch or continuous basis.

The invention is further illustrated in the following examples. Unless otherwise indicated parts and percentages are on a weight basis.

EXAMPLE I (Comparative)

Into a 9000 barrel per day continuous-reaction alkylation unit equipped with an agitator and cooling means were introduced isobutane and mixed butenes in a isobutane to mixed butene ratio of 10:1, and 92% sulfuric acid. The ratio of acid to total hydrocarbon was maintained between 1:1 to 1:2 throughout the trial period. The reactor contents were continuously mixed and the temperature in the reactor was maintained between 48° and 55° F. The effluent from the reaction vessel entered into a settling tank from which the hydrocarbon was removed as an overhead stream and the acid was removed as a bottoms stream. The acid was recycled to the reaction vessel. When the concentration of acid leaving the settling tank dropped below 92% a portion of the acid stream was dumped and replaced with sufficient fresh 99% pure sulfuric acid to adjust the acid concentration to 92%. The hydrocarbon stream was distilled to remove unreacted isobutane (which was recirculated to the reactor), leaving isooctane as the resulting substantial product. The acid consumption during this run was 0.7 lbs. per gallon of isooctane product. The average Research Octane Number (RON) of the product obtained during this run was 93.1.

EXAMPLE II

The procedure of Example I was repeated except that 500 ppm (based on the weight of sulfuric acid) of technical grade mixed neodecanoic acid having an acid number of approximately 320 is maintained in the sulfuric acid stream. The mixed neodecanoic acid used is a product of Exxon Chemicals and has a melting point of less than $-40°$ C. This product has a structure of

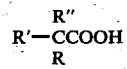

and a typical source distribution of

| | | |
|---|---|---|
| (i) | $R = CH_3$, $R' = CH_3$, $R'' = C_6H_{13}$ | ... 31% |
| (ii) | $R < C_6H_{13}$, $R' = CH_3$, $R'' > CH_3$ | ... 67% |
| (iii) | $R < C_6H_{13}$, $R' > CH_3$, $R'' > CH_3$ | ... 2% |

The acid consumption during this run was 0.6 lbs. per gallon of isooctane product. The average RON of the product obtained during this run was 94.1.

A comparison of the examples illustrates that when a small amount of mixed neodecanoic acid is added to the sulfuric acid catalyst used in an alkylation unit the acid consumption is markedly decreased. This represents a significant savings as a result of the lower acid consumption and the reduced loss of olefin as sulfate product. The examples also show that the use of mixed neodecanic acids as a catalyst promoter resulted in an increase in the RON of the product.

Although the invention is described with particular reference to specific examples it is understood that the invention includes variations. For example, other hydrocarbons, such as aromatic compounds, may be alkylated or other olefins or acids may be used. The scope of the invention is limited only by the breadth of the appended claims.

We claim:

1. In an alkylation process comprising contacting an alkylatable hydrocarbon with an olefinic alkylating agent at alkylation conditions in the presence of an acid catalyst and an alkylation promoter, the improvement comprising using as the promoter at least one carboxylic acid having the structure

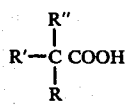

wherein R, R' and R" are the same or different alkyl groups and the average total sum of carbon atoms in R, R' and R" is 3 to 20.

2. The improved process of claim 1 wherein the average total sum of carbon atoms in R, R' and R" is 3 to 18.

3. The improved process of claim 1 wherein said alkylatable hydrocarbon is an alkane and said olefinic alkylating agent is a monoolefin.

4. The improved process of claim 3 wherein said alkane has 4 to 10 carbon atoms and said monoolefin has 3 to 10 carbon atoms.

5. The improved process of claim 4 wherein said alkane is branch-chained.

6. The improved process of any one of claims 3 to 5 wherein the concentration of alkylation promoters present in the reaction zone is about 0.0005 to 5.0 percent, based on the total weight of acid catalyst present in the reaction zone.

7. The improved process of any one of claims 3 to 5 wherein the concentration of alkylation promoter present in the reaction zone is about 0.001 to 1.0 percent, based on the total weight of acid catalyst present in the reaction zone.

8. The improved process of claim 6 wherein the average total sum of carbon atoms in R, R' and R" is 3 to 8.

9. The improved process of claim 7 wherein the average total sum of carbon atoms in R, R' and R" is 3 to 8.

10. In an alkylation process comprising contacting a saturated aliphatic hydrocarbon having 4 to 10 carbon atoms with at least one olefinic alkylating agent having 3 to 10 carbon atoms at alkylation conditions in the presence of a strong acid catalyst selected from sulfuric acid, phosphoric acid, hydrofluric acid, fluorosulfonic acid and mixtures of these and an alkylation promoter, the improvement comprising using as the alkylation promoter about 0.001 to 1.0 percent, based on the total weight of strong acid catalyst of at least one carboxylic acid having the structure

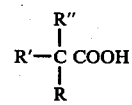

wherein R, R' and R" are the same or different alkyl groups and the average total sum of carbon atoms in R, R' and R" is 3 to 18.

11. The improved process of claim 10 wherein the average total sum of carbon atoms in R, R' and R" is 3 to 8.

12. The improved process of claim 10 wherein the sum of carbon atoms in R, R' and R" is 8.

13. The improved process of claim 10 wherein the carboxylic acid is neopentanoic acid.

14. The improved process of claim 10 wherein the carboxylic acid is a neodecanoic acid.

15. The improved process of any one of claims 10 to 14 wherein the saturated aliphatic hydrocarbon is branch-chained.

16. The improved process of claim 15 wherein the alkylation promoter is present in an amount of about 0.005 to 0.5 percent, based on the total weight of strong acid catalyst present in the reaction zone.

* * * * *